United States Patent
Breitenbach et al.

(10) Patent No.: US 9,594,073 B2
(45) Date of Patent: Mar. 14, 2017

(54) TEST SOLVENT FOR EVALUATING THE COMPATIBILITY OF BIOLOGICALLY ACTIVE SUBSTANCES AND GRAFT COPOLYMERS

(75) Inventors: Jörg Breitenbach, Mannheim (DE); Bernd Liepold, Dossenheim (DE); Jürgen Weis, Frankfurt am Main (DE)

(73) Assignee: ABBVIE DEUTSCHLAND GMBH & CO KG, Wiesbaden (DE)

( * ) Notice: Subject to any disclaimer, the term of this patent is extended or adjusted under 35 U.S.C. 154(b) by 509 days.

(21) Appl. No.: 13/578,659

(22) PCT Filed: Feb. 15, 2011

(86) PCT No.: PCT/EP2011/052230
§ 371 (c)(1),
(2), (4) Date: Jan. 28, 2013

(87) PCT Pub. No.: WO2011/101352
PCT Pub. Date: Aug. 25, 2011

(65) Prior Publication Data
US 2013/0118238 A1    May 16, 2013

(30) Foreign Application Priority Data
Feb. 18, 2010  (EP) ..................................... 10154011

(51) Int. Cl.
*G01N 33/487* (2006.01)
*C08F 283/06* (2006.01)

(52) U.S. Cl.
CPC .......... *G01N 33/487* (2013.01); *C08F 283/06* (2013.01)

(58) Field of Classification Search
CPC ............................. G01N 33/487; C08F 283/06
See application file for complete search history.

(56) References Cited

U.S. PATENT DOCUMENTS

| | | | |
|---|---|---|---|
| 4,801,460 A | 1/1989 | Goertz et al. | |
| 6,497,886 B1 * | 12/2002 | Breitenbach et al. | ........ 424/401 |
| 6,599,931 B1 | 7/2003 | Breitenbach et al. | |
| 2005/0131054 A1 * | 6/2005 | Breitenbach et al. | ........ 514/422 |
| 2008/0293828 A1 | 11/2008 | Bouillo et al. | |

FOREIGN PATENT DOCUMENTS

| | | |
|---|---|---|
| DE | 19641437 A1 | 4/1998 |
| DE | 102005053066 A1 | 5/2007 |
| EP | 0240904 81 | 7/1992 |
| EP | 0987549 B1 | 7/2012 |
| WO | 03080120 A1 | 10/2003 |
| WO | 2007051743 A3 | 7/2007 |
| WO | PCT/ISA/210 | 1/2012 |
| WO | PCT/ISA/237 | 1/2012 |

OTHER PUBLICATIONS

Chiou et al., J. Pharm. Sci. 1971, 60, 1281-1302.

* cited by examiner

*Primary Examiner* — Suzanne Ziska
*Assistant Examiner* — Thurman Wheeler
(74) *Attorney, Agent, or Firm* — Saul Ewing LLP; Peter C. Lauro, Esq.

(57) ABSTRACT

A liquid mixture, comprising a) at least one compound selected from polyols, polyol ethers wherein at least one hydroxyl group is unetherified, or polyalkylene ethers wherein at least one terminal hydroxyl group is unetherified, b) 1,3-bis(caprolactam-1-yl) butane, and c) diacetoxybutane mimics the solubility properties of a graft copolymer comprising a poly(alkylene glycol) backbone and a vinyl acetate/N-vinylcaprolactam copolymer grafted onto the backbone. In a method for evaluating the compatibility of a biologically active substance with the graft copolymer i) the biologically active sub-stance is brought into contact with the liquid mixture, and ii) the phase behavior of the test system and/or the solubility of the biologically active substance in the mixture is determined.

13 Claims, No Drawings

TEST SOLVENT FOR EVALUATING THE COMPATIBILITY OF BIOLOGICALLY ACTIVE SUBSTANCES AND GRAFT COPOLYMERS

This application is the US National Phase pursuant to 35 U.S.C. §371, of international application Ser. No. PCT/PCT/EP2011/052230, filed Feb.15, 2011, designating the United States and published in English on Aug.25, 2011 as publication WO 2011/101352 A2, which claims priority to European application Ser. No. 10154011.0, filed Feb.18, 2010. The entire contents of the aforementioned patent applications are incorporated herein by this reference.

The present invention relates to a liquid mixture serving as a test solvent, and to methods for evaluating the compatibility of biologically active substances and graft copolymers using said test solvent.

Solid dispersions, i.e. homogeneous microdisperse phases of two or more solids and the special case of so-called solid solutions (molecular dispersion systems), and their use in pharmaceutical technology are generally known, see Chiou and Riegelman J. Pharm. Sci., 60, 1281-1300 (1997). For example, the biologically active substance is dispersed in a matrix comprised of a pharmaceutically acceptable polymer. When said dispersion of the components is such that the system is chemically and physically uniform or homogeneous throughout or consists of one phase (as defined in thermodynamics), such a solid dispersion will be called a "solid solution".

Solid dispersions may be prepared by a solvent evaporation method. In a solvent evaporation method, the biologically active substance and the pharmaceutically acceptable polymer are dissolved in a common solvent and the solvent is removed from the solution obtained by evaporation. Solid dispersions may also be prepared by melt-extrusion. The melt-extrusion process comprises the steps of preparing a homogeneous melt of the biologically active substance and the pharmaceutically acceptable polymer, and cooling the melt until it solidifies. A process particularly suitable for producing solid solutions of biologically active substances is described in EP-A 0 240 904. The pharmaceutically acceptable polymers used therein are copolymers of N-vinylpyrrolidone and ethylenically unsaturated monomers.

Development of new formulations on the basis of solid solution requires testing whether the active ingredient(s) and the chosen polymer are compatible, i.e. form a homogeneous solid solution. It is likewise desirable to be able to make predictions concerning the stability of solid solutions or solid dispersions. This is because, depending on the compatibility of active ingredient and polymer, the previously homogeneous disperse phase may become inhomogeneous, or recrystallization of the active ingredient may occur. Such events which change the homogeneity of the solid solution may result in altered release characteristics and are thus unwanted. However, there is a lower limit of the amount of material required for producing melt extrudates. If the amount of active ingredient available for such tests is relatively small as it is often the case in the development phase of a new drug product, substantiated prediction on the compatibility of polymer and active ingredient requires a test method other than actually producing melt extrudates.

A system for testing compatibility of active substances and polyvinylpyrrolidone in a solid dispersion is described in EP-A 0 987 549. WO 2003/080120 describes another system which is a liquid mixture for testing compatibility of active substances and N-vinylpyrrolidone copolymers.

WO 2007/051743 discloses a graft copolymer comprising a poly(alkylene glycol) backbone and a vinyl acetate/N-vinylcaprolactam copolymer grafted onto the backbone and its use as polymeric excipient for solid dosage forms. The graft copolymer is claimed to have a high solubilisation power for a number of active ingredients. Its low glass transition temperature allows extrusion processes to be carried out at lower temperatures. The graft copolymer is commercially available as Soluplus® from BASF SE, Ludwigshafen, Germany.

The objective of the present invention is to provide a method for testing the compatibility of biologically active substances and graft copolymers comprising a poly(alkylene glycol) backbone and a vinyl acetate/N-vinylcaprolactam copolymer grafted onto the backbone.

The invention relates to a liquid mixture, comprising
a) at least one compound selected from polyols, polyol ethers wherein at least one hydroxyl group is unetherified or polyalkylene ethers wherein at least one terminal hydroxyl group is unetherified,
b) 1,3-bis(caprolactam-1-yl) butane, and
c) diacetoxybutane.

Component (a) is selected from polyols, preferably polyols having 2 or 3 carbon atoms and at least 2 hydroxyl groups, such as ethylene glycol, propylene glycol or glycerol;

polyol ethers wherein at least one hydroxyl group is unetherified, preferably polyol ethers derived from polyols having 2 or 3 carbon atoms and at least 2 hydroxyl groups wherein at least one hydroxyl group is unetherified and at least one hydroxyl group is etherified with a $C_1$-$C_4$-alkanol, such as 2-methoxyethanol or 2-ethoxyethanol; and polyalkylene ethers wherein at least one terminal hydroxyl group is unetherified, preferably poly(ethylene glycols), wherein at least one terminal hydroxyl group is unetherified and optionally one terminal hydroxyl group is etherified with a $C_1$-$C_4$-alkanol, such as poly(ethylene glycols) having a weight-average molecular mass of from 200 to 400 or poly(ethylene glycol) monoethers having a weight-average molecular mass of from 200 to 400.

Preferably, component (a) is selected from polyols, in particular glycerol.

Component (a) is either commercially available or can be prepared in a simple manner.

Methods for preparation of 1,3-Bis(caprolactam-1-yl) butane, component (b), are described in WO 98/15291, hereby incorporated by reference.

Component (c) is 1,3-diacetoxybutane or 1,4-diacetoxybutane and preferably is 1,4-diacetoxybutane. Diacetoxybutane can be obtained, for example, by esterification of 1,3-butanediol or 1,4-butanediol with acetic acid.

The term "liquid mixture" as used herein means that the mixture is liquid at 45° C. This includes mixtures that are liquid at ambient temperature or mixtures that liquefy at slightly elevated temperatures up to 45° C.

The liquid mixture preferably contains components (a), (b) and (c) in a weight ratio of [a]:[b]:[c], wherein [a] is 3-23, [b] is 47-67 and [c] is 20-40. More preferably, [a] is 8-18, [b] is 52-62 and [c] is 25-35.

The liquid mixture serves as test solvent which simulates the dissolving properties of a graft copolymer.

Accordingly, the invention further relates to a method for evaluating the compatibility of a biologically active substance with a graft copolymer comprising a polyethylene poly(alkylene glycol) backbone and a vinyl acetate/N-vinylcaprolactam copolymer grafted onto the backbone. Said method comprises (i) bringing the biologically active substance into contact with the above-defined liquid mixture to provide a test system, and (ii) determining the phase behavior of the test system and/or the solubility of the biologically active substance in the mixture.

"Compatibility" is intended to mean the ability of a substance to form a homogeneous, stable solid dispersion with the graft copolymer, this solid dispersion being in particular a solid solution, i.e. a molecular dispersion of the components in one another.

The method of the invention is carried out by first preparing a test solvent by mixing adequate amounts of components (a), (b) and (c).

In an embodiment of the method according to the invention, the graft copolymer comprises a weight proportion $x_{PEG}$ of polyethylene poly(alkylene glycol) moieties, a weight proportion $x_{VC}$ of N-vinylcaprolactam moieties and a weight proportion $x_{VA}$ of vinyl acetate moieties, and the liquid mixture comprises a weight proportion of $x_{PEG} \pm 5\%$ of component (a), a weight proportion of $x_{VC} \pm 5\%$ of component (b), and a weight proportion of $x_{VA} \pm 5\%$ of component (c).

In general, $x_{PEG}$ is from 3 to 23% by weight, usually 8 to 18% by weight; $x_{VC}$ is from 47 to 67% by weight, usually 52 to 62% by weight; $x_{VA}$ is from 20 to 40% by weight, usually 25 to 35% by weight.

Preferably, a predetermined amount of biologically active substance is mixed with the test solvent and equilibrated, e.g. by stirring with a laboratory magnetic stirrer at from 5 to 2000 rpm, or treating with ultrasound or a vortex homogenizer. Equilibration can also be speeded up by heating the test system. The heating preferably takes place in such a way that the heating rate approximately corresponds to that in a melt formulation, i.e. at from 0.5 to 5° C./min. The test system is preferably heated to a maximum of about 200° C., e.g. up to 110° C., preferably up to 70° C., e.g. to a temperature in the range from 30 to 70° C. or about to 50 to 70° C. However, heating to the boiling point of the liquid mixture is also possible in the individual case. The test system is then allowed to cool to the determination temperature, usually room temperature.

Then, the phase behavior of the test system is assessed, i.e. it is established by visual, spectroscopic and/or thermoanalytical investigation of the test system whether the biologically active substance is able to form a homogeneous phase with the liquid mixture. The assessment is carried out at a defined temperature or a series of temperatures.

Visual analysis for example a microscope such as a usual optical microscope is used. It is established in this case whether a clear solution has formed. Besides visual inspection the test system also a spectroscopic analysis is possible. For example confocal Raman spectroscopy can be used to investigate the amorphous character of the test system. Methods for thermal analysis such as differential scanning calorimetry are also suitable to assess the phase behavior of the test system. The presence of a homogeneous phase indicates that the solubility of the biologically active substance is greater than the concentration of the substance in the dissolving test. Conversely, a lower solubility can be concluded from the occurrence of a phase separation.

Preferred graft copolymers include those of poly(ethylene glycol), N-vinyl-caprolactam and vinyl acetate, especially those comprising a poly(ethylene glycol) 6000 (PEG 6000) backbone. Particularly preferred is a graft copolymer composed essentially of 3 to 23% by weight, usually 8 to 18% by weight, especially about 13% by weight, PEG 6000; 47 to 67% by weight, usually 52 to 62% by weight, especially about 57% by weight of N-vinyl-caprolactam; and 20 to 40% by weight, usually 25 to 35% by weight, especially about 30% by weight of vinyl acetate.

The graft copolymers generally have a Fikentscher K value of from 21 to 51, in particular from 31 to 41, when measured at a concentration of 1% (w/v) in ethanol.

In principle, the test system and the methods described herein are suitable for a variety of biologically active substances which include pharmaceutical active ingredients, crop protection agents, food supplements or cosmetic active ingredients. The invention is particularly useful for water-insoluble or poorly water-soluble (or "hydrophobic" or "lipophilic") compounds. Compounds are considered water-insoluble or poorly water-soluble when their solubility in water at 25° C. is less than 1 g/100 ml, especially less than 0.1 g/100 ml.

It is also possible to investigate detergents or dyes for their compatibility with the copolymers. The influence of formulation auxiliaries which are not biologically active themselves, such as sugars, sugar alcohols, solubilizers such as surfactants, or other polymeric aids, can also be investigated. For this purpose one, two or more formulation auxiliaries are included in the liquid mixture, which serves as test solvent.

In many cases, it is sufficient to state whether the solubility is greater or less than a given value. For this purpose, a predetermined amount of the biologically active substance is brought into contact with the test solvent to provide the test system. The quantitative ratios can basically be chosen freely. However, it is advisable to choose the concentration ranges in the test system such that they correspond to the active ingredient content typical of extrudate forms, i.e. generally from 0.1 to 70% by weight, preferably 10 to 30% by weight, of biologically active substance, based on the total weight of the test system.

The solubility of the biologically active substance can also be determined quantitatively, e.g. in % by weight based on the weight of test solvent and biologically active substance.

A suitable method comprises
i) providing a plurality of test systems with stepwise increasing amounts of the biologically active substance, relative to the amount of the liquid mixture, and
ii) determining the maximum amount of the biologically active substance resulting in a one-phase test system.

Preferably, the test systems are equilibrated over a defined period of time at a given temperature. The maximum amount of the biologically active substance resulting in a one-phase test system is determined, e.g. by identifying the test system which has the maximum amount of the biologically active substance and still appears as a clear solution, i.e. a single phase. The solubility of the biologically active substance is between the concentration in said one-phase test system and the test system with the next higher concentration which does not form a clear solution.

A further method comprises
i) bringing a sufficient amount of the biologically active substance into contact with the liquid mixture such that the biologically active substance dissolves incompletely in the liquid mixture to provide a two-phase test system comprised of a biologically active substance bottom and a supernatant, and
ii) determining the concentration of the biologically active substance in the supernatant.

In this method, a two-phase test system is provided with a bottom of undissolved biologically active substance and a supernatant. The concentration of the biologically active substance in the supernatant can be determined by suitable means, e. g. by high performance liquid chromatography (HPLC). The solubility of the biologically active substance is taken to be the concentration of the biologically active substance in the supernatant.

The invention also allows for predicting the storage stability of a dosage form which contains a solid solution of a biologically active ingredient in a polymer. A solid solution whose drug loading is below the solubility as determined above is assigned as likely stable against crystallization.

EXAMPLE 1

Solubility of Biologically Active Substances in Liquid Mixtures

Three liquid mixtures having the following compositions were prepared:

Mixture A: 57 wt % 1,3-bis(caprolactam-1-yl) butane; 30 wt % 1,4-diacetoxybutane; 13 wt % glycerol;

Mixture B: 57 wt % 1,3-bis(caprolactam-1-yl) butane; 30 wt % 1,4-diacetoxybutane; 13 wt % PEG400;

Mixture C: 57 wt % 1,3-bis(caprolactam-1-yl) butane; 30 wt % 1,4-diacetoxybutane; 13 wt % 1,2-diethoxyethane Fenofibrate and ibuprofen were used as the biologically active substances and their solubility in the liquid mixtures A through C was evaluated.

Samples were prepared by adding the fenofibrate or ibuprofen in portions to mixtures A, B or C until a sediment remained. The final amounts are indicated in Tables 1 and 2 ($2^{nd}$ columns). The samples were ultrasonicated at 28° C. for 15 min and then ultracentrifuged at 12,000 rpm for 20 min. Aliquots of the supernatants were diluted with a defined volume of solvent (fenofibrate samples: acetonitrile/ultrapure water pH 2.5 (70/30), ibuprofen samples: ultrapure water/acetonitrile (55/45)). The concentrations of active substance dissolved in the samples (saturation solubilities) were determined by HPLC (Waters HPLC system equipped with Waters 2487 Dual λ Absorbance Detector and Waters 2695 Separations Module) using a standard, and summarized in Tables 1 and 2 ($3^{rd}$ columns).

HPLC analyses of ibuprofen samples:

Column: LiChroCART 125-4, HPLC-Cartridge, Cat. 1.50943, LiChrospher 100, RP-18 (5 μm)

Liquid Phase: 3.8 ml 85 wt % phosphoric acid in 5 l ultrapure water/acetonitrile (55/45)

Detection at: 214 nm

Flow Rate: 2.000 ml/min

HPLC analyses of fenofibrate samples:

Column: LiChroCART 250-4, HPLC-Cartridge, Cat. 1. 50983, LiChrospher 100, RP-18 (5 μm)

Liquid Phase: acetonitrile/ultrapure water pH 2.5 (70/30)

Detection at: 286 nm

Flow Rate: 1.200 ml/min

TABLE 1

Saturation solubility of fenofibrate in liquid mixtures

| Liquid mixture | Fenofibrate added [wt %] | Saturation solubility [wt %] |
|---|---|---|
| A | 17.0 | 13.7 |
| B | 25.2 | 19.9 |
| C | 30.4 | 26.7 |

TABLE 1

Saturation solubility of ibuprofen in liquid mixtures

| Liquid mixture | Ibuprofen added [wt %] | Saturation solubility [wt %] |
|---|---|---|
| A | 59.1 | 46.1 |
| B | 52.0 | 47.6 |
| C | 54.5 | 48.2 |

EXAMPLE 2

Compatibility of Biologically Active Substances and Soluplus®

The ability of the biologically active substances fenofibrate and ibuprofen to form a homogenous solid solution in Soluplus®, a graft copolymer of 13 wt % PEG 6000, 57 wt % N-vinylcaprolactam and 30 wt % vinyl acetate moieties, was evaluated using an optical microscope.

Samples were prepared by melt extrusions of mixtures consisting of fenofibrate or ibuprofen and Soluplus®. Fenofibrate or ibuprofen was mixed with Soluplus® to yield the fenofibrate or ibuprofen concentrations indicated in tables 2 or 3. Aliquots of 50 g of the powdery mixtures were extruded on a laboratory extruder (Rondol 1 (10 mm) Rondol Technology Ltd. Staffordshire GB) using a conveying screw equipped with two kneading elements at about 120° C. and 100 rpm. The powdery mixtures were continuously metered in via a vibratory feeder. The extrudate exiting the extruder was passed through a calendar with two smooth rollers arranged at a gap distance of 0.4 mm. Calendered sheets having a thickness of about 1 mm were thus obtained.

Pieces of 2 mm×2 mm were cut out from the sheets and homogeneity of the pieces was examined using an optical microscope (Leica DMLM). Results are summarized in Tables 3 and 4.

TABLE 3

Homogenity of melt extrudates of fenofibrate and Soluplus ®

| Fenofibrate concentration [wt %] | Amount of crystals in extrudate |
|---|---|
| 11 | no crystals |
| 14 | low |
| 18 | moderate |
| 22 | moderate |
| 26 | moderate to high |

TABLE 4

Homogenity of melt extrudates of ibuprogen and Soluplus ®

| Ibuprofen concentration [wt %] | Amount of crystals in extrudate |
|---|---|
| 40 | no crystals |
| 45 | no crystals |
| 50 | low |
| 55 | moderate |
| 60 | high |

The results show that fenofibrate is capable of forming a homogeneous solid dispersion in Soluplus® up to a concentration between 11 and 14 wt %; whereas ibuprofen is capable of forming a homogeneous solid dispersion in Soluplus® up to a concentration between 45 and 50 wt %. Solubility tests in liquid mixtures A and B allow for a fair estimate of the concentration limit whereas mixture C yields too high a solubility of fenofibrate.

We claim:

1. A liquid mixture, comprising
   (a) at least one compound selected from polyols, polyol ethers wherein at least one hydroxyl group is unetherified, or polyalkylene ethers wherein at least one terminal hydroxyl group is unetherified,
   (b) 1,3-bis(caprolactam-1-yl) butane, and
   (c) diacetoxybutane,
   wherein the liquid mixture is non-aqueous and components (a), (b) and (c) are present in a weight ratio of [a]:[b]:[c] and [a] is 3-23, [b] is 47-67 and [c] is 20-40.

2. The mixture according to claim 1, wherein component (a) is selected from ethylene glycol, propylene glycol, glycerol, 2-methoxyethanol, 2-ethoxyethanolpoly-(ethylene glycols) having a weight-average molecular mass of from 200 to 400, and poly(ethylene glycol) monoethers having a weight-average molecular mass of from 200 to 400.

3. The mixture according to claim 1, wherein component (c) is 1,4-diacetoxybutane.

4. The mixture according to claim 1, wherein components (a), (b) and (c) are present in a weight ratio of [a]:[b]:[c] and [a] is 8-18, [b] is 52-62 and [c] is 25-35.

5. The mixture according to claim 1, additionally comprising at least one formulation auxiliary.

6. A method for evaluating the compatibility of a biologically active substance with a graft copolymer comprising a poly(ethylene glycol) backbone and a vinyl acetate/N-vinylcaprolactam copolymer grafted onto the backbone; the method comprising
   i. bringing the biologically active substance into contact with a non-aqueous liquid mixture according to claim 1 to provide a non-aqueous test system, and
   ii. determining the phase behavior of the non-aqueous test system and/or the solubility of the biologically active substance in the non-aqueous mixture.

7. The method according to claim 6, wherein the graft copolymer comprises a weight proportion XPEG of poly(ethylene glycol) moieties, a weight proportion xVc of N-vinylcaprolactam moieties and a weight proportion XVA of vinyl acetate moieties, and the liquid mixture comprises a weight proportion of XPEG±5% of component (a), a weight proportion of xVc±5% of component (b), and a weight proportion of XVA±5% of component (c).

8. The method according to claim 6, wherein the phase behavior of the test system is analyzed visually, spectroscopically and/or by thermal analysis.

9. The method according to claim 6, wherein the test system is heated to a temperature of up to 200° C.

10. The method according to claim 9, wherein the test system is heated to a temperature of up to 70° C.

11. The method according to claim 6, wherein the test system comprises 10 to 70 percent by weight of the biologically active substance.

12. The method according to claim 6, further comprising
   i) providing a plurality of non-aqueous test systems with stepwise increasing amounts of the biologically active substance, relative to the amount of the liquid mixture, and
   ii) determining the maximum amount of the biologically active substance resulting in a one-phase test system.

13. The method according to claim 6, further comprising
   i) bringing a sufficient amount of the biologically active substance into contact with the liquid mixture such that the biologically active substance dissolves incompletely in the liquid mixture to provide a two-phase test system comprised of a biologically active substance bottom and a supernatant, and
   ii) determining the concentration of the biologically active substance in the supernatant.

* * * * *